(12) United States Patent
Carlson et al.

(10) Patent No.: US 10,543,236 B2
(45) Date of Patent: Jan. 28, 2020

(54) ANALGESICS BASED ON SNAKE VENOMS

(71) Applicant: Natures Innovation, Inc., Buford, GA (US)

(72) Inventors: William S. Carlson, Bulford, GA (US); Michael J. Rourk, Decatur, GA (US); Holly E. Carpenter, Dawsonville, GA (US)

(73) Assignee: NATURES INNOVATION INC., Buford, GA (US)

( * ) Notice: Subject to any disclaimer, the term of this patent is extended or adjusted under 35 U.S.C. 154(b) by 158 days.

(21) Appl. No.: 14/444,403

(22) Filed: Jul. 28, 2014

(65) Prior Publication Data

US 2015/0030691 A1 Jan. 29, 2015

Related U.S. Application Data

(60) Provisional application No. 61/859,140, filed on Jul. 26, 2013.

(51) Int. Cl.
| | | |
|---|---|---|
| *A61K 35/583* | (2015.01) | |
| *A61K 36/28* | (2006.01) | |
| *A61K 36/324* | (2006.01) | |
| *A61K 36/9066* | (2006.01) | |
| *A61K 36/81* | (2006.01) | |
| *A61K 9/00* | (2006.01) | |
| *A61K 9/06* | (2006.01) | |

(52) U.S. Cl.
CPC .......... *A61K 35/583* (2013.01); *A61K 9/0014* (2013.01); *A61K 9/06* (2013.01); *A61K 36/28* (2013.01); *A61K 36/324* (2013.01); *A61K 36/81* (2013.01); *A61K 36/9066* (2013.01)

(58) Field of Classification Search
None
See application file for complete search history.

(56) References Cited

U.S. PATENT DOCUMENTS

| | | | | |
|---|---|---|---|---|
| 7,208,150 B1 * | 4/2007 | Shulov Barkan | ...... | A61K 35/58 424/172.1 |
| 7,871,647 B1 * | 1/2011 | Paradise | .............. | A61K 9/0014 424/725 |

FOREIGN PATENT DOCUMENTS

| | | | |
|---|---|---|---|
| WO | WO-1996014840 A1 | 5/1996 | |
| WO | WO-1997042944 A1 | 11/1997 | |

OTHER PUBLICATIONS

The website document entitled: "Alternative preservative and potentiator system for the personal care market" (available at http://www.cosmeticsbusiness.com/...1/article_page/Alternative_preservative_and_potentiator_system_for_the_personal_care_market/47223) Dated Dec. 18, 2006. Downloaded from website Aug. 31, 2015.*
Leeser (1958) The Britichs Homeopathic Journal, 74, 153.*
Website document entitled: "Applications and Uses of Glucono-Delta-Lactone" (available at http://www.foodchemadditives.com/application-uses). Dated Oct. 16, 2014. Downloaded from website Aug. 31, 2015).*
Website document entitled: "Lotioncrafter: Glucono Delta Lactone (GDL)" (available at http://www.lotioncrafter.com/glucono-delta-lactone-gdl.html). Downloaded from websited Aug. 31, 2015.*
Jiang et al. (2008) Toxicon 52: 638-646.*
Beaver, W.T., Mild analgesics: a review of their clinical pharmacology. The American Journal of the Medical Sciences. 1965; 251(5):576-99.
Bond, J. R. et al., Hairless Mouse Skin is Limited as a Model for Assessing the Effects of Penetration Enhancers in Human Skin. The Society for Investigative Dermatology. 1988; 90(6):810-813.
Desmeules, J. et al., Clinical pharmacology and rationale of analgesic combinations. European Journal of Anaesthesiology. 2003; 20(Supplement 28):7-12.
Doley, R. et al., Protein complexes in snake venom. Cell. Mol. Life Sci. 2009; 66:2851-2871.
Gopalakrishnakone, P. et al., Sites of action of Mojave toxin isolated from the venom of the Mojave rattlesnake. Br J Pharmacol. Jul. 1980; 69(3):421-31.
Hadgraft, J., Passive enhancement strategies in topical and transdermal drug delivery. International Journal of Pharmaceutics. 1999; 184:1-6.
Jorge, M. T. et al., Snakebite by the bushmaster (*Lachesis muta*) in Brazil: case report and review of the literature. Toxicon. 1997; 35(4):545-54.
Kim, M.-J. et al., Skin permeation enhancement of diclofenac by fatty acids. Drug Delivery. 2008; 15:373-79.
Kolesnikov, Y. et al., Analgesic synergy between topical lidocaine and topical opioids. The Journal of pharmacology and experimental therapeutics. 2000; 295(2):546-51.
Lane, M. E., Skin penetration enhancers. International Journal of Pharmaceutics. 2013; 447:12-21.
Long, L. et al., Herbal medicines for the treatment of osteoarthritis: a systematic review. Rheumatology. 2001; 40:779-93.
Macht, D. I., Experimental and Clinical Study of Cobra Venom as an Analgesic. Proc Natl Acad Sci USA. 1936; 22(1):61-71.
McCleane, G., Topic Analgesics. Anesthesiology Clin. 2007; 25:825-39.
Moore, R. A. et al., Quantitive systematic review of topically applied. British Medical Journal. 1998; 316:333-338.
Normile, D., The New Face of Traditional Chinese Medicine. Science. 2003; 299:188-190.
Patwardhan, B. et al., Ayurveda and traditional Chinese medicine: a comparative overview. eCAM. 2005; 2(4):465-73.
Reid, P. F., Cobra venom: a review of the old alternative to opiate analgesics. Alternative Therapies in Health and Medicine. 2011; 17(1):58-71.
Rokyta, D. R. et al., The genesis of an exceptionally lethal venom in the timber rattlesnake (*Crotalus horridus*) revealed through comparative venom-gland transcriptomics. BMC Genomics. 2013; 14(1)394-415.

(Continued)

*Primary Examiner* — Christopher R Tate
*Assistant Examiner* — Russell G Fiebig
(74) *Attorney, Agent, or Firm* — Keith G. Haddaway; Venable LLP

(57) ABSTRACT

A homeopathic pain topical analgesic composition based on snake venom is disclosed. The study product also contained of *Arnica montana*, a homeopathic remedy most frequently used for fractures, bruises, and muscle strains due to its analgesic and anti-inflammatory effects. The composition also contained a penetrant component to enhance penetration of the ingredients as well as an analgesic/anti-inflammatory component. The snake venoms used may include those of *Naja naja*, *Crotalus horridus* and *Lachesis muta*. A clinical study of a product formulated in this way was effective in promoting relief from muscle pain and discomfort.

9 Claims, No Drawings

(56) References Cited

OTHER PUBLICATIONS

Sanchez, E. E. et al., Disintegrin, hemorrhagic, and proteolytic activities of Mohave rattlesnake, *Crotalus scutulatus scutulatus* venoms lacking Mojave toxin. Comparative Biochemistry and Physiology, Part C. 2205; 141:124-132.

Sanz, L. et al., Snake venomics of the South and Central American Bushmasters. Comparison of the toxin composition of Lachesis muta gathered from proteomic versus transcriptomic analysis. Journal of Proteomics. 2008; 71:46-60.

Sawynok, J., Topical and Peripherally Acting Analgesics. Pharmacological Reviews. 2003; 55(1):1-20.

Tallarida, R. J., Drug Synergism: Its Detection and Applications, The Journal of Pharmacology and Experimental Therapeutics. 2001; 298(3):865-872.

Tanner, T., Delivering drugs by the transdermal route: review and comment. Skin Research and Technology. 2008; 14:249-60.

Thermo Scientific, Tech Tip#43 Technical Report: Protein Stability and Storage. Downloaded from the internet: http://www.piercenet.com/files/TR0043-Protein-storage.pdf, (3 pages).

Pierce, Technical Report/Instructions: Protein Stabilizing Cocktail. Downloaded from the internet: http://www.piercenet.com/instructions/2161759.pdf, (2 pages).

Trommer, H. et al., Overcoming the stratum corneum: the modulation of skin penetration. Skin Pharmacology and Physiology. 2006; 19, 106-21.

Wagner, H. et al., Synergy research: approaching a new generation of phytopharmaceuticals. Journal of Natural Remedies. 2009; 9(2):121-141.

Wooldridge, B.J. et al., Mojave rattlesnakes (*Crotalus scutulatus scutulatus*) lacking the acidic subunit DNA sequence lack Mojave toxin in their venom. Comp Biochem Physiol B. 2001; 130:169-179.

Zhang, P. et al., Traditional Chinese medicine in the treatment of rheumatoid arthritis: a general review. Rheumatology International. 2010; 30(6):713-718.

\* cited by examiner

ANALGESICS BASED ON SNAKE VENOMS

DESCRIPTION OF THE INVENTION

Introduction

Human beings have sought relief from bodily pain by using various preparations of naturally occurring plant and animal materials since the beginning of recorded history. From common aspirin, a derivative of willow bark extract, to more exotic substances such as the venoms of certain insects and snakes, a wide variety of substances have been found to possess analgesic and anti-inflammatory properties (1).

An important aspect of analgesia via natural substances is the route of administration. A route of administration in pharmacology and toxicology is the path by which a drug, fluid, poison, or other substance is taken into the body. Routes of administration are generally classified by the location at which the substance is applied. Common examples include oral and intravenous administration. Routes can also be classified according to where the target of action occurs. Action may be topical (local), enteral (systemic action, delivered through the gastrointestinal tract), or parenteral (systemic action, delivered by routes other than the GI tract) (2).

Another complex yet common phenomenon is that of synergy, that is, the interaction of multiple elements in a system to produce an effect different from or greater than the sum of their individual effects. Drug synergy occurs when drugs interact in ways that enhance or magnify one or more effects, or side-effects, of those drugs (3, 4). For example, combinations of analgesic drugs administered topically in some cases exhibit synergies (5).

The following disclosure explains the scientific theory behind and the practical application of a novel analgesic product. The product is designed primarily for use as a topical analgesic/anti-inflammatory for the treatment of neuropathy, arthritis, and muscular and joint pain. However, enteral administration is not precluded. Additionally, its anti-inflammatory properties may lead to additional indications.

The present invention utilizes synergies within and amongst classes of natural analgesic substances and combines these multiple interactions, in the case of topical administration, with a similar, synergistic combination of transdermal drug permeation enhancers.

Snake Venoms as Analgesic Substances

The toxic venoms of a variety of snakes have been used for centuries to treat a wide variety of ailments by Ayurvedic, folk and homeopathic systems of medicine. Allopathic medicine officially became aware of the use of snake venom as an analgesic as early as 1936 with the publication of Dr. David I. Macht's study using cobra venom reconstituted in physiological saline to relieve the pain of cancer patients. Dr. Macht delivered up to a maximum of five "mouse units" to each patient by either intramuscular or subcutaneous injection. In order to be clear various terms should be defined to explain Dr. Macht's procedure. Dr. Macht took the dried raw venom and then reconstituted it in physiological saline (0.9% sodium chloride) at a ratio of 1 unit dried venom to 10,000 units of saline. In homeopathic terms, this would correspond to a 4× dilution. He then sterilized the solution with low temperature heat (60° C.). One mouse unit is equivalent to "the minimum dose required to kill a mouse (of 20 to 22 gm) within twenty hours after intraperitoneal injection", or about 0.01 mg dried venom apparently delivered in a 100 microliter bolus (6).

Snake venom is modified saliva secreted by the salivary glands. Broadly speaking, snake venoms were considered either "neurotoxic" or "cytotoxic." Generally, neurotoxic venoms disrupt conduction of nerve signals so that the prey animal succumbs to paralysis of respiration or heart failure. In most cases cytotoxic venoms act on the vascular system resulting in death from hemolysis, coagulation or hemorrhage. Actually, snake venoms contain a mixture of several different toxins with some species producing venoms that primarily act on the nervous system while other species have venoms that primarily act on the blood or vascular system. In the inventive analgesic product, we use a combination of two or more of the venoms selected from four different venomous snakes. Each different venom is known to possess analgesic and/or anti-inflammatory properties which operate via distinguishably different biochemical pathways. The presence of multiple venoms from different snakes in solution leads to a synergistic effect between venoms to enhance the analgesic effects resulting from multiple neurotoxic agents present in the formulation while actually limiting dangerous toxic properties. The four snakes employed are the Indian cobra (*Naja naja*), the timber rattlesnake (*Crotalus horridus*), the South American Bushmaster (*Lachesis muta*), and the Mojave rattlesnake (*Crotalus scutulatus scutulatus*). The composition of the venoms and the biochemistry of their actions are discussed below.

Indian Cobra (*Naja naja*)

Cobra venom is a complex, viscous mixture which contains various proteins and enzymes that serve to immobilize prey victims or to serve as a defense mechanism against potential predators (7, 8). Cobras produce around 0.3 mL (300 mg) of venom per milking, and the lethal injection dose of venom in humans is around 15 mg (1 mg/kg is the lethal dose in most mammals) (8). Cobras can inject 50-100 mg following a bite and these large doses result in neurotoxic effects that lead to respiratory failure/paralysis and rapid death in prey.

The active components of the venom represent between 20-25% of the actual venom and they are responsible for the neurotoxic effects observed (8). The principal components of the venom are neurotoxic peptides which target the nicotinic cholinergic system and act as antagonists to nicotinic acetylcholine receptors (NAchRs). NAchRs are sodium gated ion channels in neurons which regulate neuronal activity, and these receptors are activated by the neurotransmitter acetylcholine or the stimulant drug nicotine. The analgesic effect of cobra venom peptides is a result of antagonism or blockage of various NAchRs in the body. These receptors normally function to transmit neuronal signals and their activity in certain tissues (such as muscle) leads to the feeling of pain. When a very low dose of venom is administered (approximately $10^{-9}$ to $10^{-4}$ dilution from whole venom administered orally (less than 0.55 mg/kg), or less than 4 mg (0.061 mg/kg) doses via injection, cobra venom peptides may bind to NAchRs to block their function with pain signals deceasing as a result of the interaction between the neurotoxin and the neuronal receptors (8). The effects of cobra venom may be longer lasting than the effects of morphine and the venom effects may take longer than opiate analgesics to reach the desired outcome (8). Some components of cobra venom have anti-inflammatory effects in addition to their analgesic effects (GATX for example). Characteristics of cobra venom components are listed in the following table:

| Venom Components | | | |
|---|---|---|---|
| Name | Physiological Effect | Mechanistic Activity | Size/MW* |
| Cobrotoxin (COTX) | Analgesic | α1 NAchR antagonist | 6.7 kDa, 60 aa |
| Cobratoxin (CATX) | Analgesic, anti-inflammatory | α1, 7, 8, 9 NAchR antagonist; cytokines | 7.8 kDa, 71 aa |
| Najanalgesin | Analgesic | | 6.7 kDa |
| Cobra venom factor | Anti-inflammatory, immune | Complement activating protein | 149 kDa, glycoprotein |
| NTX1 | Analgesic | | 1.2 kDa |
| Nigexine | Cytotoxicity | Phospholipase activity | 14 kDa, 119 aa |

*Size/MW values are approximate

Timber Rattlesnake (*Crotalus horridus*)

The Type A venom of the timber rattlesnake is characterized by snake-venom serine proteinases (200-300 amino acids (aa) in length, 30-40 kDa), phospholipase A2 (canebrake toxin) proteins (200-300 aa, 30-40 kDa), bradykinin-potentiating peptides (5-13 aa, Pro and PyroGlu rich), and C-type natriuretic peptides (20 aa) (9, 10).

Snake venom serine proteases are responsible for degradation of fibrinogen which affects blood clotting in the victim. A lack of fibrinogen results in hemorrhage. These serine proteases may act as enzymes or they may exert their toxic effects by simply binding to receptors at the junctions of motor neurons (resulting in muscle paralysis in the victim).

Phospholipase A2 (PLA2) proteins are mainly responsible for binding to receptors at the site of neuromuscular junctions and for degrading the cell membranes of the neurons through enzymatic activity. PLA2 proteins block neurotransmission by interfering with neuronal signaling in multiple ways. PLA2 proteins also exert their toxic function by means of PLA2 protein complexes. The specific PLA2 protein, known as canebrake toxin, found in Type A *C. horridus* venom exerts a neurotoxic effect rather than a hemorrhagic effect (10).

Bradykinin-potentiating peptides stimulate bradykinin function and result in vasodilation and cause a subsequent drop in blood pressure. C-type natriuretic peptides also affect blood volume through vasodilation effects (9-11). The following table provides additional information on the venom of the timber rattlesnake:

| Type A Venom | | | |
|---|---|---|---|
| Components Name | Physiological Effect | Mechanistic Activity | Size/MW* |
| Serine Proteinases | Analgesic | Neuromuscular effects | 30-40 kDa, 200-300 aa |
| Phospholipase A$_2$ (PLA$_2$, Canebrake toxin) | Analgesic | Neuromuscular effects | 30-40 kDa, 200-300 aa |
| Bradykinin-potentiating peptides | Vasodilation, anti-inflammatory | | 1.5 kDa, 5-13 aa |
| C-type natriuretic peptides | Vasodilation, anti-inflammatory | | 2.7 kDa, 10-20 aa |

*Size/MW values are approximate.

South American Bushmaster (*Lachesis muta*)

Bushmaster venom is a complex mixture of enzymes, proteins, and peptides with dramatic hemorrhagic, coagulant, and neurotoxic venom effects on the victim. Bushmasters are large snakes and can inject around 300 mg of venom in a single bite (12, 13). These large doses result in neurotoxic effects that lead to respiratory failure/paralysis and rapid death of prey. The composition of bushmaster venom is similar to the venom of the timber rattlesnake in composition. However, in contrast to rattlesnake venom, bushmaster venom is rich in metalloproteinase enzymes. Bushmaster venom is rich in $Zn^{2+}$-metalloproteinases (30-110 kDa, 200-800 aa), snake-venom serine proteinases (200-300 aa, 30-40 kDa), phospholipase A2 proteins (PLA2), bradykinin-potentiating peptides (5-13 aa), and C-type natriuretic peptides (10-20 aa) (13). Metalloproteinases affect blood clotting and often result in tissue damage and bleeding at the site of the bite. They may also act at neuromuscular junctions to affect neuronal function. Metalloproteinases are $Zn^{2+}$ dependent so EDTA should be avoided in the formulation due to its metal chelating function which would inactivate these enzymes (12-14). The following table summarizes the information on bushmaster venom:

| Venom Components | | | |
|---|---|---|---|
| Name | Physiological Effect | Mechanistic Activity | Size/MW* |
| Metalloproteinases | Analgesic | Neuromuscular effects | 30-110 kDa, 200-800 aa |
| Serine Proteinases | Analgesic | Neuromuscular effects | 30-40 kDa, 200-300 aa |
| Phospholipase A$_2$ (PLA$_2$) | Analgesic | Neuromuscular effects | 30-40 kDa, 200-300 aa |
| Bradykinin-potentiating peptides | Vasodilation, anti-inflammatory | | 1.5 kDa, 5-13 aa |
| C-type natriuretic peptides | Vasodilation, anti-inflammatory | | 2.7 kDa, 10-20 aa |

*Size/MW values are approximate.

Mojave Rattlesnake (*Crotalus scutulatus scutulatus*)

The Type A venom of the Mojave rattlesnake is rich in a protein known as Mojave toxin (15, 16). The Mojave toxin has powerful neurotoxic effects due to its presynaptic phospholipase action on the neurons. The Mojave toxin protein is composed of an acidic subunit and a basic subunit which interact through non-covalent interactions (16). The basic subunit is mainly responsible for the neurotoxic effects although the presence of the acidic subunit in complex in mature Mojave toxin has a stronger toxic effect than the basic subunit alone (17). Although most *C. s. scutulatus* snakes have Mojave toxin in their venom, there are populations of these snakes in some areas of central Arizona that do not have the toxin present. (18) These snakes have venom (Type B) which is predominantly hemorrhagic in nature and is rich in metalloproteinase and disintegrin proteins (18).

| | Type A Venom Component(s) | | |
|---|---|---|---|
| Name | Physiological Effect | Mechanistic Activity | Size/MW* |
| Phospholipase A$_2$ (PLA$_2$, Mojave toxin) | Analgesic | Neuromuscular effects, neurotoxin | 30-40 kDa, 200-300 aa (2 subunits) |

*Size/MW values are approximate.

The following table presents a summary of the various venoms used in the present invention:

| Scientific name | Common Name | Unique Neurotoxic Agents |
| --- | --- | --- |
| *Naja naja* | Indian Cobra | Cobrotoxin (COTX) |
| | | Cobratoxin (CATX) |
| | | Najanalgesin |
| | | Cobra venom factor |
| | | NTX1 |
| | | Nigexine |
| *Crotalus horridus* | Timber Rattlesnake | Canebrake toxin |
| | | Rattlesnake serine proteinases |
| *Lachesis muta* | South American Bushmaster | Neurotoxic metalloproteinases |
| | | Pit viper serine proteinases |
| | | Phospholipase $A_2$ ($PLA_2$) |
| *Crotalus scutulatus scutulatus* | Mojave Rattlesnake | Mojave toxin |

Custom Protein Stabilizing Matrix

Due to the heterogeneous and protein-rich nature of snake venoms, special considerations have been addressed in our formulations to support the three dimensional conformation and related activity of the proteins and enzymes found in the snake venoms. For long term storage, proteins usually require a pH stabilizing buffer and/or a crowding agent, such as bovine serum albumin (BSA) (19), and our novel analgesic product concept is no exception. Several commercial preparations are available, such as the Protein Stabilizing Cocktail made by Pierce Biotechnology, Inc. (20). However, we decided to avoid any potential protein-protein interactions between BSA and snake venom proteins and to also avoid the use of EDTA as a trace metal sequestering agent.

Therefore, in our formulation methyl cellulose (methocel) a commercially available, high purity polysaccharide serves as the crowding agent. The hydrophilic and hydrophobic regions of this cellulose-based molecule allow proteins to adhere and likely prevents misfolding and inactivation of the proteins. The methocel may also prevent protein binding to the storage vessel and resulting surface denaturation as proteins would be more likely to associate with the methocel itself. Other natural polysaccharide crowding agents could also conceivably be used such as gellans, carrageenans, pectins, other celluloses and agars.

With a pH (around 7) and ionic strength conditions of the formulations comparable to living tissue, the proteins are more likely to remain in their active conformations. The proteins and peptides found in snake venom vary widely in size, structure, and amino acid sequence. Snake venom proteins are inherently robust in structure and function and contain (in many cases) several covalent disulfide bridges that strongly support their three dimensional architectures and promote maintenance of their activity in a formulation (11). The proteins found in snake venom exert their toxic effects mostly through binding interactions rather than enzymatic activity, such as in the case of the canebrake toxin from the timber rattlesnake, so that as long as the snake venom proteins remain mostly intact they should be able to exert activity at neuromuscular junctions. Many of these proteins form complexes with other proteins to exert their full activity (11).

The metalloproteinase proteins found in bushmaster venom are $Zn^{2+}$-dependent, so EDTA should be avoided in the formulation due to its metal chelating function. As an alternative to EDTA, the trace metal sequestering agent glucono-delta-lactone (D-Glucono-1,5-lactone) is used in the formulation at a very low concentration. Since glucono-delta-lactone is also a mild acidulant and a neutral pH is desired, the mildly basic, broad spectrum antimicrobial agent benzalkonium chloride (BZK) will also be used in the formulation at a very low concentration in order to form a pH neutral buffer solution.

Allopathic and Natural Analgesic/Anti-Inflammatory Component

The second component of the new and novel analgesic product concept described herein is a synergistic combination of two or more substances known to possess analgesic and/or anti-inflammatory properties from either of the following two categories:

1) Allopathic or modern pharmaceutical substances including but not limited to nonsteroidal anti-inflammatory drugs, opioids, capsaicin (from *Capsicum*), local anesthetics, antidepressants, glutamate receptor antagonists, alpha-adrenoceptor agonists, adenosine, cannabinoids, cholinergic receptor agonists, GABA agonists, neuropeptides or antagonists for inflammatory mediators (prostanoids, bradykinin, ATP, biogenic amines, and nerve growth factor) (21-23).

2) Natural or herbal analgesic and anti-inflammatory medicines from any of the major folk or indigenous traditions including but not limited to Native American herbal remedies, traditional Chinese medicine (TCM), Ayurvedic medicine, the Tibetan Medical System or the Siddha medicinal system. Example ingredients include ashwagandha (*Withania somnifera*), frankincense (*Boswellia serrata*), turmeric (*Curcuma longa*), avocado/soybean unsaponifiables (ASU), Devil's claw (*Harpagophytum procumbens*), Java grass (*Cyperus rotundus*) Guduchi (*Tinospora cordifolia*), Saussurea lappa, Picrorhiza kurro, ginger (*Zingiber officinale*), feverfew (*Tanacetum parthenim*), American aspen (*Populus tremuloides*), yarrow (*Achillea millefolium*), European ash (*Fraxinus excelsior*), European goldenrod (*Solidago virgaurea*), and stinging nettle (*Urtica dioica*) (24-27).

Multiple Drug Synergies

Multiple drug synergies are complex phenomena, and much has been written on the subject in the scientific literature (28, 29). Most combinations of drugs require empirical clinical evidence before any substantive conclusions can be drawn. However, some general guidelines have been established. According to one researcher, "combination analgesics can play a valuable role in pain management. However, dubious combinations (directed against the same targets or with unwanted interactions) and 'old fashioned' fixed dose multiple analgesic agent combinations should be avoided." (30). The preceding sections on the biochemistry of each of the snake venoms demonstrate that those agents are not directed at the same targets. Additionally, as will be shown in our example formula, our new and novel analgesic product incorporates a margin of safety in the form of lower than 'old fashioned' fixed dosages of the individual drugs if they were administered separately.

Transdermal Penetration Enhancement

The final feature of our new analgesic product is the use of several complementary transdermal permeation enhancing ingredients in the formulation (31-33). Penetration enhancers can be generally grouped into the following categories: water; sulfoxides and similar chemicals; Azone (1-dodecylazacycloheptan-2-one); pyrrolidinones; fatty acids; alcohols, fatty alcohols and glycols; surfactants; urea; essential oils (e.g. linalool (2,6-dimethyl-2,7-octadien-6-ol)); terpenes and terpenoids; and phospholipids (34). In fact, one recent scientific literature review found more than 275 chemical compounds cited as penetration enhancers from more than 400 sources (35). Methylsulfonylmethane (MSM), a sulfone from the sulfoxides and other chemicals category, is a well-known permeability enhancer that has been used to treat or prevent osteoarthritis (36). However, we are combing it with the powerful synergistic combination of propylene glycol, isopropyl alcohol and oleic acid (glycols category, alcohols category, and fatty acid category) (37, 38). Finally, a small amount of menthyl lactate is added for its combination of analgesic and permeation enhancing properties (39, 40). It will be appreciated that these additives greatly enhance to local effect of our product when topically applied.

Conclusion

The new analgesic product described above has the following features;
1. A synergistic combination of bioactive snake venoms using dilutions of $10^{-3}$ to $10^{-10}$ (homeopathic 3× to 10×).
2. A unique preservation system for the combination of venoms in an aqueous mileu at room temperature.
3. A synergistic combination of established analgesic/anti-inflammatory agents from a wide variety of medical systems.
4. A synergistic combination of transdermal permeation enhancing ingredients.

Five example formulation of our new and novel analgesic product follow:

Sample formulation #1

| Ingredient | Range |
| --- | --- |
| Water | 31-34% |
| *Naja naja* venom 5X | 0.1-0.001 |
| *Lachesis muta* venom 6X | 0.1-0.001 |
| *Crotalus horridus* venom 6X | 0.1-0.001 |
| Propylene glycol | 42-45% |
| Oleic acid | 1-3% |
| Isopropyl alcohol | 3-6% |
| Menthyl lactate | 1-3% |
| *Capsicum* 2X | 0.1-0.001% |
| *Boswellia* 3X | 0.1-0.001% |
| *Arnica* 1X | 0.5-2.0% |
| Methocel | 1-3% |
| BZK | 0.1-0.3% |
| Glucono-delta-lactone | 0.1-0.3% |
| *Curcuma longata* 5X | 0.1-0.001% |

Sample formulation #2

| Ingredient | Range |
| --- | --- |
| Water | 40-42% |
| *Naja naja* venom 5X | 0.1-0.0001% |
| *Lachesis muta* venom 6X | 0.1-0.0001% |
| *Crotalus horridus* venom 6X | 0.1-0.0001% |
| Propylene glycol | 42-45% |
| MSM | 5-8% |
| Oleic acid | 1-3% |
| Isopropyl alcohol | 3-6% |
| Menthyl lactate | 1-3% |
| *Capsicum* 2X | 0.1-0.001% |
| *Boswellia* 3X | 0.1-0.001% |
| *Arnica* 1X | 0.5-2.0% |
| Methocel | 1-3% |
| BZK | 0.1-0.3% |
| Glucono-delta-lactone | 0.1-0.001% |
| *Curcuma longata* 5X | 0.1-0.001% |

Sample formulation #3

| Ingredient | Range |
| --- | --- |
| Water | 30-33% |
| *Naja naja* venom 7X | 0.1-2.0% |
| *Lachesis muta* venom 8X | 0.1-2.0% |
| *Crotalus horridus* venom 8X | 0.1-2.0% |
| Propylene glycol | 42-45% |
| MSM | 5-8% |
| Oleic acid | 1-3% |
| Isopropyl alcohol | 3-6% |
| Menthyl lactate | 1-3% |
| *Capsicum* 2X | 0.1-0.001% |
| *Boswellia* 3X | 0.1-0.001% |
| *Arnica* 1X | 0.5-2.0% |
| Methocel | 1-3% |
| BZK | 0.1-0.3% |
| Glucono-delta-lactone | 0.1-0.001% |
| *Curcuma longata* 5X | 0.1-0.001% |

Sample formulation #4

| Ingredient | Range |
| --- | --- |
| Water | 35-38% |
| *Naja naja* venom 5X | 0.1-0.0001%% |
| *Lachesis muta* venom 6X | 0.1-0.0001%% |
| *Crotalus horridus* venom 6X | 0.1-0.0001% |
| Propylene glycol | 42-45% |
| MSM | 5-8% |
| Linalool | 1-3% |
| Menthyl lactate | 0.1-2.0% |
| *Capsicum* 2X | 0.1-0.001%% |
| *Boswellia* 3X | 0.1-0.001%% |
| *Arnica* 1X | 0.5-2.0% |
| Methocel | 1-3% |
| BZK | 0.1-0.3% |
| Glucono-delta-lactone | 0.1-0.001% |
| *Curcuma longata* 5X | 0.1-0.001% |

Sample formulation #5

| Ingredient | Range |
| --- | --- |
| Water | 35-38% |
| *Naja naja* venom 5X | 0.1-0.001% |
| *Lachesis muta* venom 6X | 0.1-0.001% |
| *Crotalus horridus* venom 6X | 0.1-0.001% |
| Propylene glycol | 42-45% |
| MSM | 5-8% |
| Oleic acid | 1-3% |
| Isopropyl alcohol | 3-6% |
| *Populus tremula* (5:1) 6X | 0.1-2.0% |
| *Fraxinus excelsior* (5:1) 3X | 0.1-2.0% |
| *Solidago virgaurea* (5:1) 2X | 0.1-2.0% |
| Methocel | 1-3% |
| BZK | 0.1-0.3% |
| Glucono-delta-lactone | 0.1-0.001% |

A standard clinical study was undertaken to compare the effectiveness of a product (similar to formula #1, above) against a placebo in which the snake venoms were omitted. This randomized, double-blind, placebo-controlled study was designed to demonstrate the efficacy of the formula in alleviating muscle pain by assessing validated scales for pain and discomfort. Safety and tolerability of the study product was also evaluated through adverse event analysis. Healthy volunteers age 18 to 65 years of age with occasional muscular discomfort (level 5/10 or more) for at least 4 days out of the week were included in the study. Thirty five subjects were screened and 23 were randomized to receive the formula or placebo. 20 subjects completed the study, 12 from the active group and 8 from the placebo group.

The active and the placebo groups demonstrated a significant difference in the 0-10 Numeric Pain Rating Scale at week 2. Moreover, pain rating was also significantly decreased by 32.14% compared to baseline at week 2.

The data also noted significantly reduced morning and evening muscle pain compared to baseline values in the active product group. Morning pain was significantly reduced by 26.34% while evening pain was significantly lowered by 29.40% after 2 weeks of topical application (twice daily) of the study product.

These findings suggest that the study product consisting of snake venom was effective in promoting relief from muscle pain and discomfort. Snake venom has been used as treatment of chronic pain. The study product also contained of *Arnica montana*, a homeopathic remedy most frequently tested. It is commonly used for fractures, bruises, and muscle strains due to its analgesic and anti-inflammatory effects. However, available clinical studies on *Arnica* did not demonstrate the clinical efficacy on moderating muscle pain as well as accompanying symptoms of muscle dysfunction. The study product did not lead to clinically significant changes in vital signs and no adverse events were noted to be related to study product.

The following table shows that the formula was statistically more effective than the placebo at relieving pain.

| Endpoint | Time Point | Change | Significance | p-value |
| --- | --- | --- | --- | --- |
| 0-10 Numeric Pain Scale Rating | Week 2 Comparison Between Active and Placebo | Lower for Active Group | Significant | 0.047 |
| 0-10 Numeric Pain Scale Rating | Change from Baseline to Week 2 Comparison Between Active and Placebo | Greater Decrease for Active Group | Near Significant | 0.098 |
| 0-10 Numeric Pain Scale Rating | Comparison of Baseline and Week 2 within Active Group | Decreased from Baseline | Significant | 0.001 |
| Reduction of Discomfort in the Morning | Comparison of Baseline and Week 1 within Active Group | Decreased from Baseline | Significant | 0.000 |
| Reduction of Discomfort in the Morning | Comparison of Baseline and Week 2 within Active Group | Decreased from Baseline | Significant | 0.000 |
| Reduction of Discomfort in the Morning | Comparison of Baseline and Week 1 within Placebo Group | Decreased from Baseline | Significant | 0.005 |
| Reduction of Discomfort in the Morning | Comparison of Baseline and Week 2 within Placebo Group | Decreased from Baseline | Near Significant | 0.052 |
| Reduction of Discomfort in the Evening | Comparison of Baseline and Week 1 within Active Group | Decreased from Baseline | Significant | 0.000 |
| Reduction of Discomfort in the Evening | Comparison of Baseline and Week 2 within Active Group | Decreased from Baseline | Significant | 0.000 |
| Reduction of Discomfort in the Evening | Comparison of Baseline and Week 1 within Placebo Group | Decreased from Baseline | Significant | 0.005 |
| Reduction of Discomfort in the Evening | Comparison of Baseline and Week 2 within Placebo Group | Decreased from Baseline | Significant | 0.001 |

This randomized, double-blind clinical trial reported that a combination of various snake venoms were effective in reducing muscle joint pain and discomfort. In this two week study, effects on joint pain were not as pronounced as effects on muscle pain. Perhaps, a longer study period is needed to assess chronic joint pain. Further human clinical and animal studies are necessary to fully elucidate the mechanism of action of snake venom proteins.

REFERENCES

1. Gold, H., Cattell, M. & Beaver, W. T. Mild Analgesics: A Review of Their Clinical Pharmacology. *The American Journal of the Medical Sciences* 250, (1965).
2. http://en.wikipedia.org/wiki/Route_of_administration
3. Tallarida, R. J. Drug Synergism: Its Detection and Applications. *J Pharmacol Exp Ther* Sep. 1, 2001 298:865-872
4. http://en.wikipedia.org/wiki/Drug_synergy#Drug_synergy
5. I. Kolesnikov, Y. a, Chereshnev, I. & Pasternak, G. W. Analgesic synergy between topical lidocaine and topical opioids. *The Journal of pharmacology and experimental therapeutics* 295, 546-51 (2000).
6. Macht, D I. Experimental and Clinical Study of Cobra Venom as an Analgesic. *Proc Natl Acad Sci USA*. 1936; 22(1):61-71.
7. http://en.wikipedia.org/wiki/Indian_cobra
8. Reid, P. Cobra Venom: A Review of the Old Alternative to Opiate Analgesics. *Alternative Therapies* 2011, Vol. 17, 1, pgs. 58-71.
9. http://en.wikipedia.org/wiki/Crotalus_horridus (the Type A venom)
10. Rokyta, D. R. et al. The genesis of an exceptionally lethal venom in the timber rattlesnake (*Crotalus horridus*) revealed through *comparative* venom-gland transcriptomics. *BMC Genomics*. 2013, 14(1), pg. 394.
11. Doley, R. and Kini, R. M. Protein complexes in snake venom. *Cell. Mol. Life Sci*. (2009) 66:2851-2871
12. http://en.wikipedia.org/wiki/Lachesis_muta
13. Sanz, L. et al. Snake venomics of the South and Central American Bushmasters. Comparison of the toxin composition of *Lachesis muta* gathered from proteomic versus transcriptomic analysis. *Journal of Proteomics*. 2008, 71, pg. 46-60.
14. Jorge, M. T. et al. Snakebite by the bushmaster (*Lachesis muta*) in Brazil: case report and review of the literature. *Toxicon*. 1997, 35(4):545-54.
15. http://en.wikipedia.org/wiki/Crotalus_scutulatus
16. Sanchez, E. E. et al. Disintegrin, hemorrhagic, and proteolytic activities of Mohave rattlesnake, *Crotalus scutulatus scutulatus* venoms lacking Mojave toxin. *Comparative Biochemistry and Physiology*, Part C 141 (2005) 124-132.
17. Gopalakrishnakone, P. et al. Sites of action of Mojave toxin isolated from the venom of the Mojave rattlesnake. *Br J Pharmacol*. 1980 July; 69(3):421-31.
18. Wooldridge B J, Pineda G, Banuelas-Ornelas J J, Dagda R K, Gasanov S E, Rael E D, Lieb C S: Mojave rattlesnakes (*Crotalus scutulatus scutulatus*) lacking the acidic subunit DNA sequence lack Mojave toxin in their venom. *Comp Biochem Physiol B*. 2001, 130:169-179.
19. Thermo Scientific. Tech Tip#43 Technical Report: Protein Stability and Storage. http://www.piercenet.com/files/TR0043-Protein-storage.pdf, Retrieved 2013.
20. Thermo Scientific. Technical Report/Instructions: Protein Stabilizing Cocktail. http://www.piercenet.com/instructions/2161759.pdf, Retrieved 2013.
21. Sawynok, J. Topical and Peripherally Acting Analgesics. *Pharmacological Reviews* 55, 1-20 (2003).

22. Moore, R. A., Carroll, D., Wiffen, P. J. & Mcquay, H. J. Quantitive systematic review of topically applied. *British Medical Journal* 316, 333-338 (1998).
23. McCleane, G. Topical analgesics. *Anesthesiology clinics* 25, 825-39, vii (2007).
24. Peng Zhang, Jun Li, Yong Han, Xiao Wei Yu, Ling Qin; Traditional Chinese medicine in the treatment of rheumatoid arthritis: a general review. *Rheumatology International*, April 2010, Volume 30, Issue 6, pp 713-718
25. Long, L., Soeken, K. & Ernst, E. Herbal medicines for the treatment of osteoarthritis: a systematic review. *Rheumatology* (Oxford, England) 40, 779-93 (2001).
26. Epidemiologists, T. O. The New Face of Traditional Chinese Medicine. *Science* 299, 188-190 (2003).
27. Patwardhan, B., Warude, D., Pushpangadan, P. & Bhatt, N. Ayurveda and traditional Chinese medicine: a comparative overview. *Evidence-based complementary and alternative medicine*: eCAM 2, 465-73 (2005).
28. Wagner, H. Synergy research: approaching a new generation of phytopharmaceuticals. *Fitoterapia* 82, 34-7 (2011).
29. Tallarida, R. J. Drug Synergism: Its Detection and Applications. *The Journal of Pharmacology and Experimental Therapeutics* 298, 865-872 (2001).
30. Desmeules, J., Rollason, V., Piguet, V. & Dayer, P. Clinical pharmacology and rationale of analgesic combinations. *European journal of anaesthesiology*. Supplement 28, 7-11 (2003).
31. Hadgraft, J. Passive enhancement strategies in topical and transdermal drug delivery. International journal of pharmaceutics 184, 1-6 (1999).
32. Tanner, T. & Marks, R. Delivering drugs by the transdermal route: review and comment. Skin research and technology: official journal of International Society for Bioengineering and the Skin (ISBS) [and] International Society for Digital Imaging of Skin (ISDIS) [and] International Society for Skin Imaging (ISSI) 14, 249-60 (2008).
33. Trommer, H. & Neubert, R. H. H. Overcoming the stratum corneum: the modulation of skin penetration. A review. Skin pharmacology and physiology 19, 106-21 (2006).
34. Lane, M. E. Skin penetration enhancers. International journal of pharmaceutics 447, 12-21 (2013).
35. Osborne, D. W., Henke, J. J. Skin Penetration Enhancers Cited in the Technical Literaure *Pharmaceutical Technology* November 1977, 58-66.
36. http://en.wikipedia.org/wiki/Methylsulfonylmethane
37. Kim, M.-J. et al. Skin permeation enhancement of diclofenac by fatty acids. *Drug delivery* 15, 373-9 (2008).
38. Bond, J. R., Barry, W. Hairless Mouse Skin is Limited as a Model for Assessing the Effects of Penetration Enhancers in Human Skin *The Society for Investigative Dermatology*, 1988, (90)6, Jun. 1988, 810-813
39. Patent application, Use of menthyl lactate as a pain reliever, WO 1996014840 A1.
40. Patent application, Topical composition, WO 1997042944 A1

What is claimed is:

1. A topical analgesic composition consisting of:
   (A) an aqueous preservation vehicle;
   (B) a venom component;
   (C) a non-venom analgesic or anti-inflammatory component; and
   (D) a penetrant component;
   wherein the aqueous preservation vehicle consists essentially of:
      31-42% water,
      1-3% methyl cellulose,
      0.001-0.3% glucono-delta-lactone, and
      0.1-0.3% benzalkonium chloride;
   wherein the venom component consists essentially of:
      0.0001-0.1% of a 5× dilution of *Naja naja* venom,
      0.0001-0.1% of a 6× dilution of *Crotalus horridus* venom, and
      0.0001-0.1% of a 6× dilution of *Lachesis muta* venom;
   wherein the non-venom analgesic or anti-inflammatory component consists of at least two analgesic and/or anti-inflammatory substances selected from allopathic pharmaceutical substances and natural analgesic or anti-inflammatory substances directed to a different target than the venom component;
   wherein the penetrant component consists essentially of:
      42-45% propylene glycol,
      1-3% oleic acid,
      3-6% isopropyl alcohol, and
      at least one of 1-3% menthyl lactate or 5-8% Methylsulfonylmethane (MSM); and
   wherein the percentages are based on the amount in the composition as a whole.

2. The topical analgesic composition of claim 1, wherein the non-venom analgesic or anti-inflammatory component consists of:
   0.1-0.001% of a 2× dilution of capsaicin,
   0.1-0.001% of a 3× dilution of frankincense,
   0.5-2.0% of a 1× dilution of *Arnica Montana*, and
   0.1-0.001% of a 5× dilution of turmeric.

3. The topical analgesic composition of claim 1, wherein the non-venom analgesic or anti-inflammatory component consists of:
   0.1-2.0% of a 6× dilution of aspen (5:1),
   0.1-2.0% of a 3× dilution of ash (5:1), and
   0.1-2.0% of a 2× dilution of goldenrod (5:1).

4. The topical analgesic composition of claim 1, wherein the penetrant consists of:
   42-45% propylene glycol,
   1-3% oleic acid,
   3-6% isopropyl alcohol, and
   1-3% menthyl lactate.

5. The topical analgesic composition of claim 1, wherein the penetrant consists of:
   42-45% propylene glycol,
   1-3% oleic acid,
   3-6% isopropyl alcohol,
   1-3% menthyl lactate, and
   5-8% MSM.

6. The topical analgesic composition of claim 1, wherein the penetrant consists of:
   42-45% propylene glycol,
   1-3% oleic acid,
   3-6% isopropyl alcohol, and
   5-8% MSM.

7. A topical analgesic composition consisting of:
   (A) an aqueous preservation vehicle;
   (B) a venom component;
   (C) a non-venom analgesic or anti-inflammatory component; and
   (D) a penetrant component;
   wherein the aqueous preservation vehicle consists essentially of:
      31-42% water,
      1-3% methyl cellulose,
      0.001-0.3% glucono-delta-lactone, and
      0.1-0.3% benzalkonium chloride;
   wherein the venom component consists essentially of:
      0.0001-0.1% of a 5× dilution of *Naja naja* venom,
      0.0001-0.1% of a 6× dilution of *Crotalus horridus* venom, and
      0.0001-0.1% of a 6× dilution of *Lachesis muta* venom;

wherein the non-venom analgesic or anti-inflammatory component consists of at least two analgesic and/or anti-inflammatory substances selected from allopathic pharmaceutical substances and natural analgesic or anti-inflammatory substances directed to a different target than the venom component;

wherein the penetrant component consists essentially of:
42-45% propylene glycol,
0.1-2% methyl lactate,
1-3% linalool, and
5-8% Methylsulfonylmethane (MSM); and wherein the percentages are based on the amount in the composition as a whole.

8. The topical analgesic composition of claim 7, wherein the non-venom analgesic or anti-inflammatory component consists of:
0.1-0.001% of a 2× dilution of capsaicin,
0.1-0.001% of a 3× dilution of frankincense,
0.5-2.0% of a 1× dilution of *Arnica Montana*, and
0.1-0.001% of a 5× dilution of turmeric.

9. The topical analgesic composition of claim 7, wherein the non-venom analgesic or anti-inflammatory component consists of:
0.1-2.0% of a 6× dilution of aspen (5:1),
0.1-2.0% of a 3× dilution of ash (5:1), and
0.1-2.0% of a 2× dilution of goldenrod (5:1).

* * * * *